United States Patent
Yasui

(10) Patent No.: US 11,275,024 B2
(45) Date of Patent: Mar. 15, 2022

(54) METHOD FOR ESTIMATING PRODUCTION LOCATION

(71) Applicant: Nippon Telegraph and Telephone Corporation, Tokyo (JP)

(72) Inventor: Takako Yasui, Tokyo (JP)

(73) Assignee: Nippon Telegraph and Telephone Corporation, Tokyo (JP)

(*) Notice: Subject to any disclaimer, the term of this patent is extended or adjusted under 35 U.S.C. 154(b) by 0 days.

(21) Appl. No.: 16/979,665

(22) PCT Filed: Mar. 12, 2019

(86) PCT No.: PCT/JP2019/009952
§ 371 (c)(1),
(2) Date: Sep. 10, 2020

(87) PCT Pub. No.: WO2019/176925
PCT Pub. Date: Sep. 19, 2019

(65) Prior Publication Data
US 2021/0025817 A1    Jan. 28, 2021

(30) Foreign Application Priority Data

Mar. 13, 2018  (JP) .............................. JP2018-045288
Oct. 30, 2018  (JP) .............................. JP2018-203823

(51) Int. Cl.
*G01N 21/39* (2006.01)
*G01N 1/44* (2006.01)
*G01N 33/483* (2006.01)

(52) U.S. Cl.
CPC ............... *G01N 21/39* (2013.01); *G01N 1/44* (2013.01); *G01N 33/4833* (2013.01); *G01N 2201/06113* (2013.01)

(58) Field of Classification Search
CPC ...... G01N 21/39; G01N 1/44; G01N 33/4833; G01N 2201/06113
See application file for complete search history.

(56) References Cited

FOREIGN PATENT DOCUMENTS

| | | |
|---|---|---|
| CN | 202053164 U | 11/2011 |
| JP | 2006189351 A | 7/2006 |
| JP | 2015224901 A | 12/2015 |
| JP | 2017219428 A | 12/2017 |
| WO | 2016063918 A1 | 8/2017 |

OTHER PUBLICATIONS

"Stable Isotope Ratio Analysis for Assessing the Authenticity of Food of Animal Origin" published in Comprehensive Reviews in Food Science and Food Safety, vol. 15, 2016 by Federica Camin. (Year: 2016).*

"Laboratory and Field Methods for Stable Isotope Analysis in Human Biology" published in American Journal of Human Biology 27:593-604 (2015) by Laurie J. Reitsema. (Year: 2015).*

(Continued)

*Primary Examiner* — Jamil Ahmed
(74) *Attorney, Agent, or Firm* — Slater Matsil, LLP

(57) ABSTRACT

The stable isotope ratios of carbon and hydrogen contained in a measurement target object collected from an animal are measured. An area in which the animal has grown is estimated from the measured stable isotope ratios of carbon and hydrogen (S3).

9 Claims, 10 Drawing Sheets

(56) References Cited

OTHER PUBLICATIONS

Picarro, Product Explanatory Materials, Internet <URL: http://www.bristol.ac.uk/media-library/sites/cabot/migrated/documents/measuring-co2-1.pdf>, May 2013, Searched on Oct. 3, 2018, 28 pages. As discussed in specification.

Picarro, "Geographical Analysis of Olive Oil Samples Originating from Eight Countries Using Picarro's Novel Simultaneous 13C + D CM-CRDS Isotope Analyzer", Picarro Application Notes, AN029, 2011, 6 Pages.

Matusbara et al., "Stable Isotope Analysis in Avian Ecology", Journal of the Yamashina Institute for Ornithology, vol. 30, 1998, pp. 59-82. As discussed in specification.

Nakashita et al. "Carbon and nitrogen stable isotope evidence for the involvement of a captured Asiatic black bear in damages at a rainbow trout farm", 2007, vol. 47, No. 1, pp. 19-23.

Nakashita et al., "Investigation of Habitat History Using Carbon and Nitrogen Stable Isotopes in Asiatic Black Bears Captured and Killed", Pro Natura Fund, 14th Grant Performance Report, 2005, pp. 113-120. As discussed in specification.

Yoshimura, et al., "Stable Isotope Ratio Analysis Using Laser Gas Sensing Technology and Its Applications," Papers of the Institute of Electronics, Information and Communication Engineers, vol. J100-C, No. 8, Jul. 2017, pp. 310-315.

Yoshimura et al. "High Sensitivity Laser Gas Sensing Technology and Application of Isotope Ratio Analysis", NTT Technical Journal, vol. 26, No. 2, Feb. 2014, pp. 27-30. As discussed in the specification.

Bowen, "Waterisotopes.org", Internet <URL: http://wateriso.utah.edu/waterisotopes/pages/data_access/oipc.html>, University of Uta, Searched on Oct. 3, 2018, 1 page. As discussed in the specification.

Saad, Nabil, Ph.D., "Geographical Analysis of Olive Oil Samples Originating from Eight Countries Using Picarros Novel Simultaneous 13C + D CM-CRDS Isotope Analyzer," Application Note, 2011, Picarro, Inc. Santa Clara, CA, 4 pages.

Kagaku, "Multiple Stable Isotope Analyses for Verifying Geographical Origin and Agricultural Practice of Japanese Rice Samples", vol. 58, No. 12, 2009, pp. 1053-1058. As discussed in the specification.

Suzuki, "Development of determination method for the geographical origin of agricultural products using chemical analysis", Lecture abstracts of the 65th conference of Japan Association of Food Preservation Science, Japan Association of Food Preservation Science, Jun. 25, 2016, pp. 27-30.

Yoshimura, "A Study for Atmospheric Water Circulation Processes by Applying Stable Isotopic Information", Tokyo University Graduate School Doctoral Dissertation, 2002, 4 pages. As discussed in specification.

Yoshimura et al. The Meteorological Society of Japan, Meteorological Research Note No. 220, 2009, 2 pages. As discussed in the specification.

Yan Zhao et al., "Recent developments in application of stable isotope analysis on agro-product authenticity and traceability," Food Chemistry, 145, 2014, pp. 300-305.

Rumiko Nakashita et al., "Stable carbon, nitrogen, and oxygen isotope analysis as a potential tool for verifying geographical origin of beef," Analytica Chimica Acta, 617, 2008, pp. 148-152.

\* cited by examiner

METHOD FOR ESTIMATING PRODUCTION LOCATION

CROSS-REFERENCE TO RELATED APPLICATIONS

This application is a national phase entry of PCT Application No. PCT/JP2019/009952, filed on Mar. 12, 2019, which claims priority to Japanese Application No. 2018-045288, filed on Mar. 13, 2018 and Japanese Application No. 2018-203823, filed on Oct. 30, 2018 which applications are hereby incorporated herein by reference.

TECHNICAL FIELD

The present invention relates to a geographical origin estimation method of estimating the geographical origin of a measurement target object collected from an animal.

BACKGROUND

Animal hair products are available as products using hair collected from animals as materials. Of these animal hair products, cashmere fibers collected from cashmere goats have unique superior properties and are dealt with at high prices. Among the cashmere fibers, cashmere fibers collected from cashmere goats having grown in specific brand areas such as the Alxa district and the Chifeng district in China are high-class materials and dealt with at particularly high prices.

Recently, however, geographical origin deception, by which clothes and the like using cashmere fibers collected in geographical origins other than these specific brand area as raw materials are so labeled that they are manufactured by using cashmere fibers collected from cashmere goats having grown in the brand areas, occurs and poses a problem. To prevent cashmere fiber geographical origin deception like this, a scientific geographical origin determination method is being desired.

As for labeling of clothes, a testing method using optical microscopy is recently defined by the Japanese Industrial Standards "JIS L1030 (Mixture Ratio Testing Method for Fiber Products)" as fiber discrimination or a fiber mixture ratio testing method. Optical microscopy uses the outer appearance of hair as the clue of discrimination. Optical microscopy is useful because a cashmere goat and other animals have different hair fiber surfaces. However, cashmere goats of the same kind have very similar outer appearances of hair, so the geographical origin is difficult to discriminate.

Recently, a discrimination method using DNA and a method of specifying the type of animal hair by directly analyzing protein as a main component of animal hair have also been proposed (see, e.g., patent literature 1). However, the both methods can discriminate the difference between animal species, but cannot discriminate the difference between growth areas of the same kind of cashmere goats having grown in different areas, and specify the respective growth areas of these cashmere goats.

As a method of estimating a geographical origin, a technique that uses the stable isotope ratios of elements constituting a target has been reported. For example, the stable isotope ratios of oxygen and hydrogen are used to estimate the geographical origins of grains (see, e.g., non-patent literatures 1 and 2). The stable isotope ratios of oxygen and hydrogen contained in precipitation (rain) have geographical dependence. The stable isotope ratios of oxygen and hydrogen constituting a crop grown by using rain having fallen on the land as growth water also show geographical dependence similar to that of precipitation.

On the other hand, there is a study indicating that the relation between the stable isotope ratios of nitrogen and carbon and the feeding habit is high for feathers (see, e.g., non-patent literature 3). There is also a study indicating that the relation between the stable isotope ratio of carbon and the feeding habit is high for an Asiatic black bear, by changing the feeds to corn as a C4 plant and barley as a C3 plant in each arbitrary period, and checking the stable isotope ratio of carbon contained in hair grown in the period (see, e.g., non-patent literature 4). In either study, however, no result indicating the relation between the stable isotope ratio of carbon and the geographical origin is obtained.

At present, therefore, the method using the stable isotope ratio is limited to the estimation of the geographical origins of grains. Accordingly, the present situation is that there is no method of easily estimating the geographical origin of a measurement target object such as animal hair collected from an animal.

RELATED ART LITERATURE

Patent Literature

Patent Literature 1: International Publication No. 2013/154208A1
Patent literature 2: Japanese Patent Laid-Open No. 2010-276466

Non-Patent Literature

Non-Patent Literature 1: Suzuki, Nakashita, and Korenaga: "Multiple Stable Isotope Analyses for Verifying Geographical Origin and Agricultural Practice of Japanese Rice Samples", BUNSEKI KAGAKU, Vol. 58, No. 12, pp. 1053-1058, 2009
Non-Patent Literature 2: Yoshimura, Koutoku, Fujii, Sakamoto, and Sakai: "High Sensitivity Laser Gas Sensing Technology and Application of Isotope Ratio Analysis", NTT Technical Journal, Vol. 26, No. 2, pp. 27-30, 2014
Non-Patent Literature 3: Matusbara and Minami: "Stable Isotope Analysis in Avian Ecology", Journal of the Yamashina Institute for Ornithology, vol. 30, pp. 59-82, 1998
Non-Patent Literature 4: Nakashita and Hayashi: "Investigation of Habitat History Using Carbon and Nitrogen Stable Isotopes in Asiatic Black Bears Captured and Killed", PRO NATURA FUND, 14th Grant Performance Report, pp. 113-120, 2005
Non-Patent Literature 5: "Picarro Product Explanatory Materials", [Searched on Oct. 3, 2018], Internet <URL: http://www.bristol.ac.uk/media-library/sites/cabot/migrated/documents/measuring-co2-1.pdf>
Non-Patent Literature 6: Kei YOSHIMURA, "A Study for Atmospheric Water Circulation Processes by Applying Stable Isotopic Information", Tokyo University Graduate School Doctoral Dissertation, 2002
Non-Patent Literature 7: Kei YOSHIMURA, Kimpei ICHIYANAGI, and Atsuko SUGIMOTO, 2009: The Meteorological Society of Japan, Meteorological Research Note No. 220
Non-Patent Literature 8: "Waterisotopes.org", [Searched on Oct. 3, 2018], Internet <URL: http://wateriso.utah.edu/waterisotopes/pages/data_access/oipc.html>.

SUMMARY

Disclosure of Embodiments of the Invention

Problem to be Solved by Embodiments of the Invention

It is an object of the present invention to provide a geographical origin estimation method capable of easily estimating a measurement target object collected from an animal.

Means of Solution to the Problem

A geographical origin estimation method includes a first step of measuring a stable isotope ratio of carbon contained in a measurement target object collected from an animal, a second step of measuring a stable isotope ratio of a constituent element of water contained in the measurement target object, and a third step of estimating an area where the animal has grown from the measured stable isotope ratios of carbon and the constituent element of water.

Effect of Embodiments of the Invention

Embodiments of the present invention makes it possible to easily estimate the geographical origin of a measurement target object.

DETAILED DESCRIPTION OF ILLUSTRATIVE EMBODIMENTS

Best Mode for Carrying Out Embodiments of the Invention

An embodiment of the present invention will be explained in detail below with reference to the accompanying drawings.

Principle of Embodiment

A geographical origin estimation method as one embodiment of the present invention is characterized by estimating the growth area of an animal from the stable isotope ratios of carbon and a constituent element of water contained in a measurement target object collected from the animal.

Figure 1:
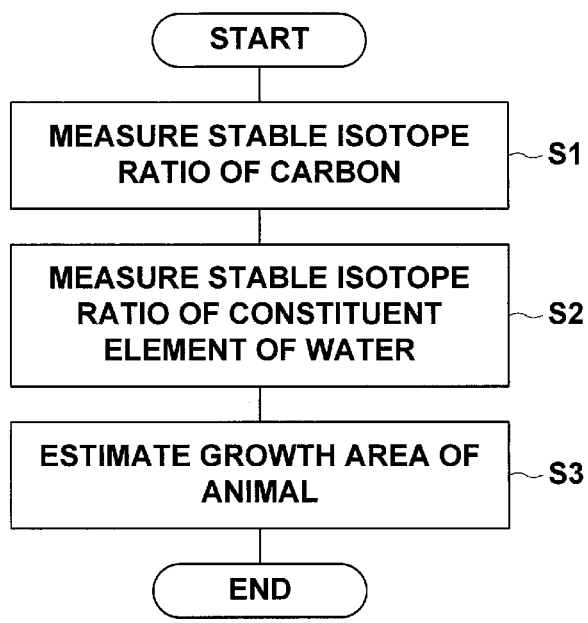
FIG. 1 is a flowchart showing the procedure of a geographical origin estimation method as one embodiment of the present invention.

More specifically, as shown in FIG. 1, this geographical origin estimation method includes step S1 of measuring the stable isotope ratio of carbon contained in a measurement target object, step S2 of measuring the stable isotope ratio of a constituent element of water contained in the measurement target object, and step S3 of estimating the growth area of the animal from which the measurement target object was collected from the measured stable isotope ratios of carbon and the constituent element of water. Note that the constituent element of water is hydrogen or oxygen. In step S2, the stable isotope ratio of one of hydrogen and oxygen need only be measured. In step S3, the estimation need only be performed by using the measured stable isotope ratio of hydrogen or oxygen.

An experiment to be described later revealed that the stable isotope ratio of a constituent element of water contained in a measurement target object collected from an animal depends on the stable isotope ratio of a constituent element of water drunk by the animal. Water drunk by an animal is water of precipitation in the area. The stable isotope ratio of a constituent element of water contained in precipitation has an area dependence. Accordingly, the stable isotope ratio of a constituent element of water contained in a measurement target object collected from an animal shows the area dependence. It was, therefore, found by research conducted by the inventor of embodiments of the present invention that the growth areas of an animal can be narrowed down from the stable isotope ratio of a constituent element of water contained in a measurement target object collected from the animal.

Also, as will be apparent from another experiment to be described later, the stable isotope ratio of carbon contained in a measurement target object collected from an animal depends on the kind of a plant eaten by the animal. The present inventor focused on the fact that a plant or feed eaten by an animal changes in accordance with the growth area of the animal. That is, it was found that the growth areas of an animal eating a given plant can be narrowed down by estimating the kind of the plant from the stable isotope ratio of carbon and checking the distribution of habitats of the plant.

The important point of this geographical origin estimation method is to narrow down, based on the above findings, the growth areas of an animal, from which a measurement target object is collected, by using the stable isotope ratios of a plurality of elements.

Figure 2:
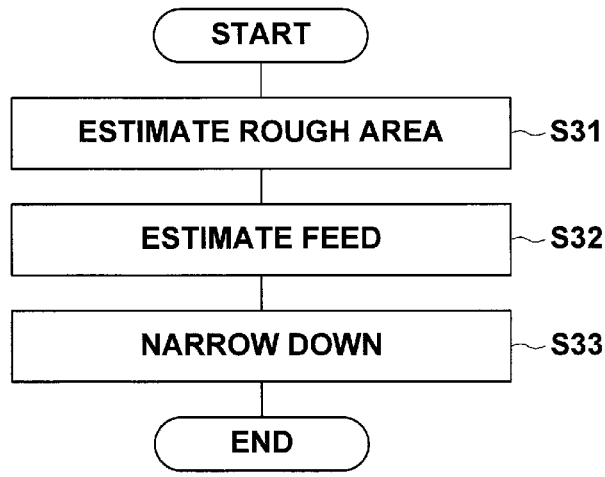
FIG. 2 is a flowchart showing a detailed procedure of an estimation step.

Based on the above-described principle, step S3 of estimating the growth area of an animal can be executed by a procedure shown in FIG. 2. First, a rough growth area of the animal is estimated from the stable isotope ratio of the constituent element of water measured in step S2 (step S31). Feed used to grow the animal is estimated from the stable isotope ratio of carbon measured in step S1 (step S32). The rough area estimated in step S31 is narrowed down to an area using the feed estimated in step S32, and the narrowed-down area is estimated as the growth area of the animal (step S33).

When a database indicating the relationship between the stable isotope ratios of both carbon and a constituent element of water and the growth area of an animal is prepared beforehand, it is possible to immediately obtain the estimation result of the growth area of the animal from the measurement results of the stable isotope ratios of carbon and the constituent element of water in steps S1 and S2. However, if this database is formed by taking account of areas using feed, the estimation method using the database is practically the same as the estimation method including steps S31 to S33.

Note that step S1 of measuring the stable isotope ratio of carbon and step S2 of measuring the stable isotope ratio of the constituent element of water described above can be executed in the order of steps S1 and S2 or vice versa, i.e., in the order of steps S2 and S1. If possible, the stable isotope ratios of carbon and hydrogen may also be measured in parallel by simultaneously executing steps S1 and S2.

Definition of Stable Isotope Ratio

Next, the definition of the stable isotope ratio will be explained. The ratios of nonradioisotopes existing in nature are used as the stable isotope ratios of carbon and hydrogen to be measured in this embodiment. The ratio of $^{12}C$ to $^{13}C$ is used as the stable isotope ratio of carbon. The ratio of $^{1}H$ to $D(^{2}H)$ is used as the stable isotope ratio of hydrogen. However, each of these stable isotope ratios is normally expressed not as an absolute ratio but as a $\delta$ value as a millesimal deviation from the isotope ratio of a standard sample.

The stable isotope ratio of carbon can be indicated as $\delta^{13}C$ by equation (1) below. The stable isotope ratio of hydrogen can be indicated as $\delta D$ by equation (2) below. Note that in these equations, SAMP indicates the isotope ratio in an analytical sample, and STD indicates the isotope ratio in a standard sample.

$$\delta^{13}C = \left\{ \frac{(^{13}C/^{12}C)_{SAMP}}{(^{13}C/^{12}C)_{STD}} - 1 \right\} \times 1000 \, (0/00) \quad (1)$$

$$\delta D = \left\{ \frac{(D/^{1}H)_{SAMP}1}{(D/^{1}H)_{STD}} - 1 \right\} \times 1000 \, (0/00) \quad (2)$$

A standard sample of the stable isotope ratio of hydrogen is normally represented by using VSMOW (Vienna Standard Mean Ocean Water). A standard sample of the stable isotope ratio of carbon is normally represented by using VPDB (Vienna Pee Dee Belemnite).

Measurements of Stable Isotope Ratios

The measurements of the stable isotope ratios will be explained below. Animal hairs of 10 animals of the same kind grown in the same stock farm by being fed with grass classified as a C3 plant are prepared as samples. In this embodiment, the hairs of cashmere goats are used as the animal hairs.

The stable isotope ratio of carbon of each of these 10 prepared animal hair samples is measured by using laser spectroscopic stable isotope ratio analysis. First, a carbon dioxide gas is generated by burning the 10 animal hair samples. The generated carbon dioxide gas is irradiated with a laser beam. The stable isotope ratio of carbon is measured by measuring and analyzing the laser beam absorption amount (the optical absorption intensity) by laser spectroscopy.

Figure 3:
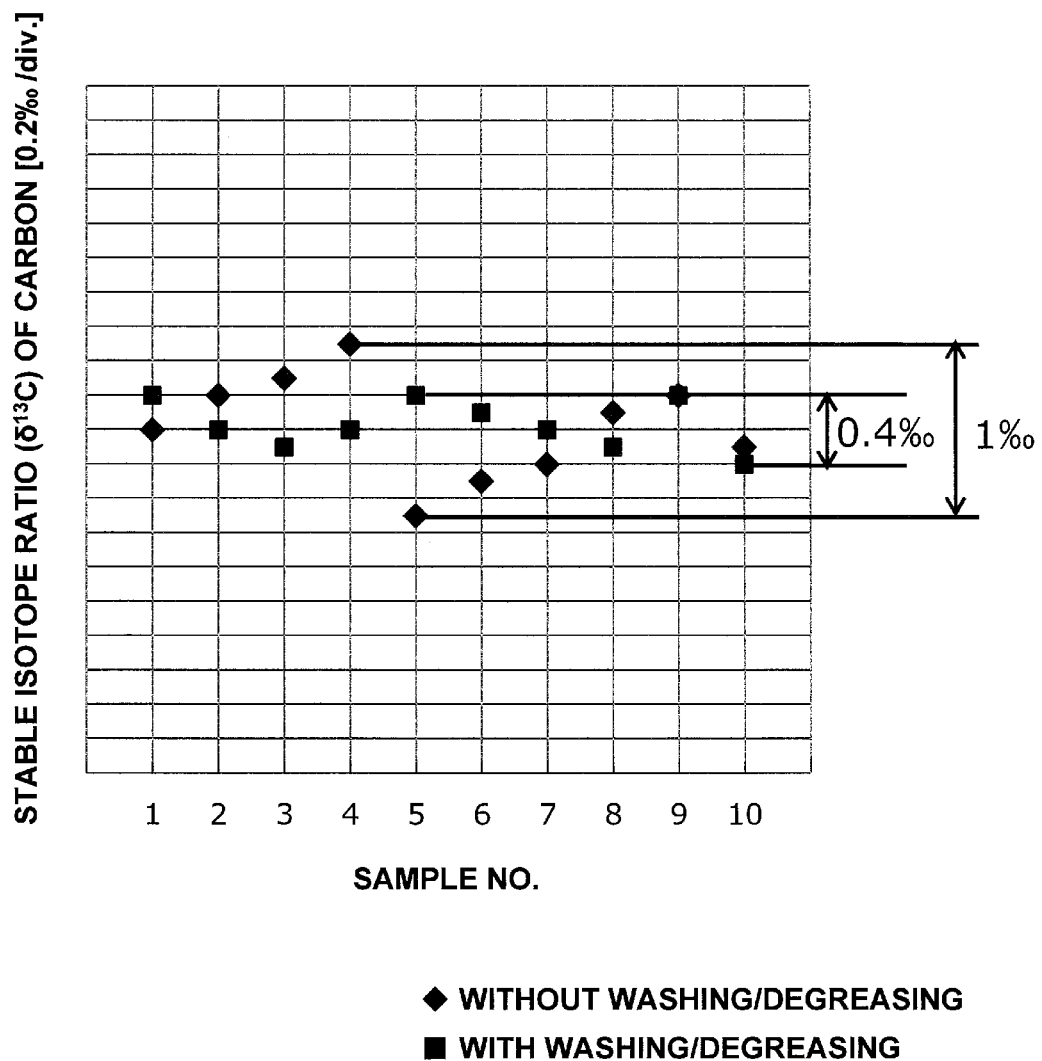
FIG. 3 is a graph comparing the stable isotope ratios of carbon contained in animal hairs of different individuals in accordance with the presence/absence of a pre-process.

The measurement value thus obtained is the stable isotope ratio for all carbon elements contained in, e.g., an organic substance (keratin) forming the animal hair and dirt sticking to the animal hair. Rhombic points in FIG. 3 indicate the measurement results. A maximum individual difference between the stable isotope ratios of carbon of the animal hairs of sample Nos. 1 to 10 was 1‰.

On the other hand, a pre-process is performed to remove dirt such as sebum and dandruff from the abovementioned 10 animal hair samples. First, the 10 animal hair samples are washed with an arbitrary neutral detergent. The washed 10 animal hair samples are dried. A degreasing process is performed by dipping the dried 10 animal hair samples in ethanol for 10 min. The stable isotope ratio of carbon of each degreased sample is analyzed by laser spectroscopic stable isotope ratio analysis.

By thus washing and degreasing the animal hair, carbon contained in the dirt sticking to the animal hair is removed. This makes it possible to measure the stable isotope ratio of only carbon contained in an organic substance (e.g., keratin) sticking to the animal hair. Square points in FIG. 3 indicate the measurement results. By washing and degreasing the animal hair, the individual difference between the stable isotope ratios of carbon decreased to 0-4‰ or less. This shows that in animals of the same kind grown in the same stock farm by being fed with the same feed, the stable isotope ratios of carbon contained in an organic substance (e.g., keratin) forming the animal hair have almost the same value.

Figure 4:
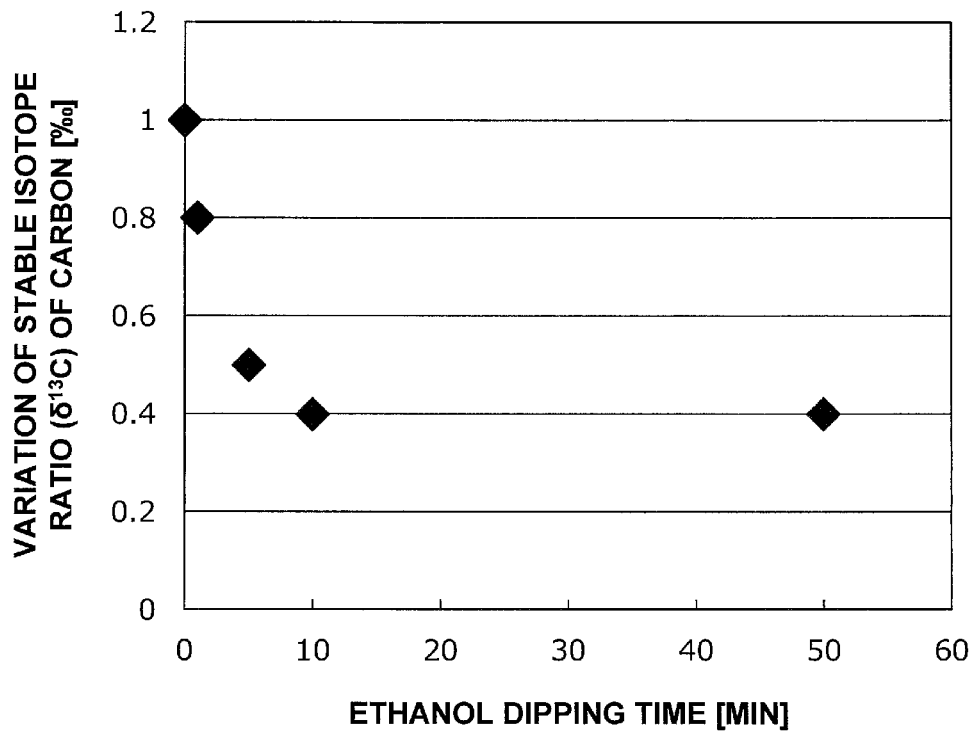
FIG. 4 is a graph showing results obtained by measuring the stable isotope ratio of carbon by changing an ethanol dipping time.

FIG. 4 shows the results of measurements of the stable isotope ratios of carbon performed by changing the ethanol dipping time. When the ethanol dipping time is prolonged, the individual variations between the stable isotope ratios of carbon reduce, and become constant when the time is to min or more. When the ethanol dipping time is to min or more, therefore, carbon contained in dirt sticking to animal hair is completely removed, so the stable isotope ratio of only carbon contained in an organic substance forming the animal hair can be measured.

Like the stable isotope ratio of carbon, the stable isotope ratio of hydrogen can also be analyzed by laser spectroscopic stable isotope ratio analysis. While animal hair samples are stored and transported, however, the animal hair samples absorb hydrogen atoms contained in the surrounding environment as water, so the stable isotope ratio of hydrogen of each animal hair sample changes with time. In addition, the animal hair samples absorb washing water used when washing the animal hair samples and containing a neutral detergent, and this sometimes influences the measurement result of the stable isotope ratio of hydrogen of each animal hair sample. This makes it difficult to estimate a geographical origin by comparison of the stable isotope ratios of hydrogen. To prevent this, water in the animal hair samples is removed by vaporization by using freeze-drying. Consequently, it is possible to measure only the stable isotope ratio of hydrogen contained in an organic substance forming each animal hair sample.

Figure 5:
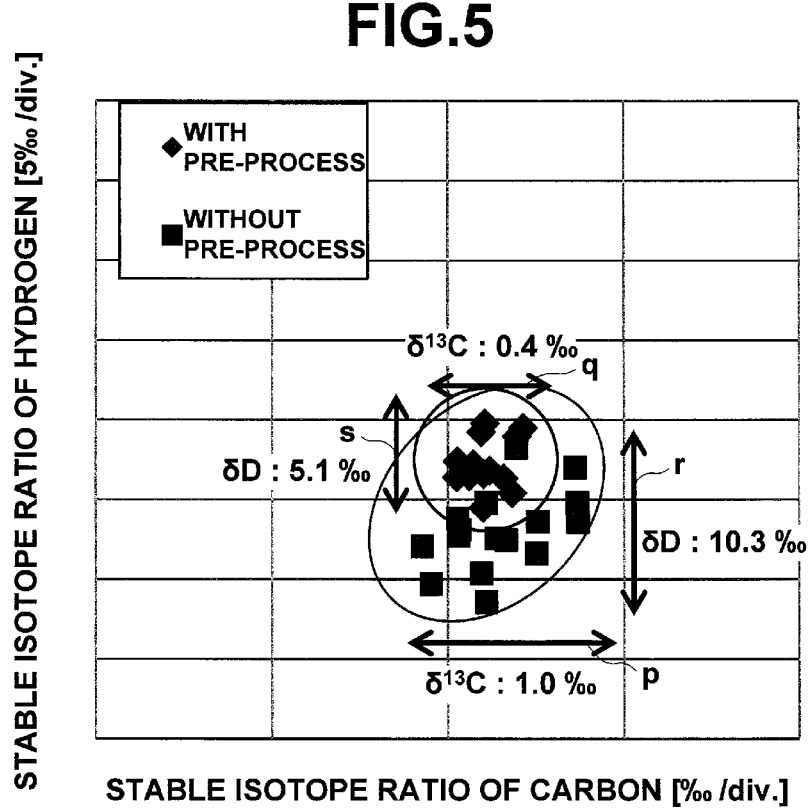
FIG. 5 is a graph showing the measurement results of the stable isotope ratios of carbon and oxygen when a pre-process was performed and was not performed.

FIG. 5 shows the measurement results of the stable isotope ratios of carbon and hydrogen when a pre-process was performed and was not performed. As the pre-process, animal hair samples were degreased with ethanol for 10 min, and then freeze-dried at a temperature of −50° C. and a vacuum degree of 8 Pa for 6 hrs. In FIG. 5, rhombic points indicate the measurement results when the pre-process was performed, and the square points indicate the measurement results when the pre-process was not performed.

As indicated by symbol p, the variation of the stable isotope ratios ($\delta^{13}C$) of carbon was 1‰ when the degreasing process (ethanol treatment) was not performed. On the other hand, as indicated by symbol q, the variation of the stable isotope ratios ($\delta^{13}C$) of carbon was 0-4‰ when the degreasing process (ethanol treatment) was performed. Accordingly, the degreasing process reduced the variation produced by the individual differences between the stable isotope ratios of carbon from 1‰ to 0.4‰.

As indicated by symbol r, the variation of the stable isotope ratios ($\delta D$) of hydrogen was 10.3‰ when the freeze-drying process was not performed. On the other hand, as indicated by symbol s, the variation of the stable isotope ratios ($\delta D$) of hydrogen was 5.1‰ when the freeze-drying process was performed. Accordingly, the freeze-drying process reduced the variation produced by the individual differences between the stable isotope ratios of hydrogen from 10.3‰ to 5.1‰. These pre-processes make it possible to measure the stable isotope ratios of hydrogen and carbon of animal hair samples in the same geographical origin more accurately.

Estimation of Feed from Stable Isotope Ratio of Carbon

Animal hair sample A of an animal grown by being fed with grass classified as a C3 plant as feed, animal hair sample B of an animal grown by being fed with both feed containing a plant classed as a C4 plant such as corn and grass classified as a C3 plant as feed, and animal hair sample C of an animal grown by being fed with a plant classified as the C4 plant such as corn as feed are prepared.

Figure 6:
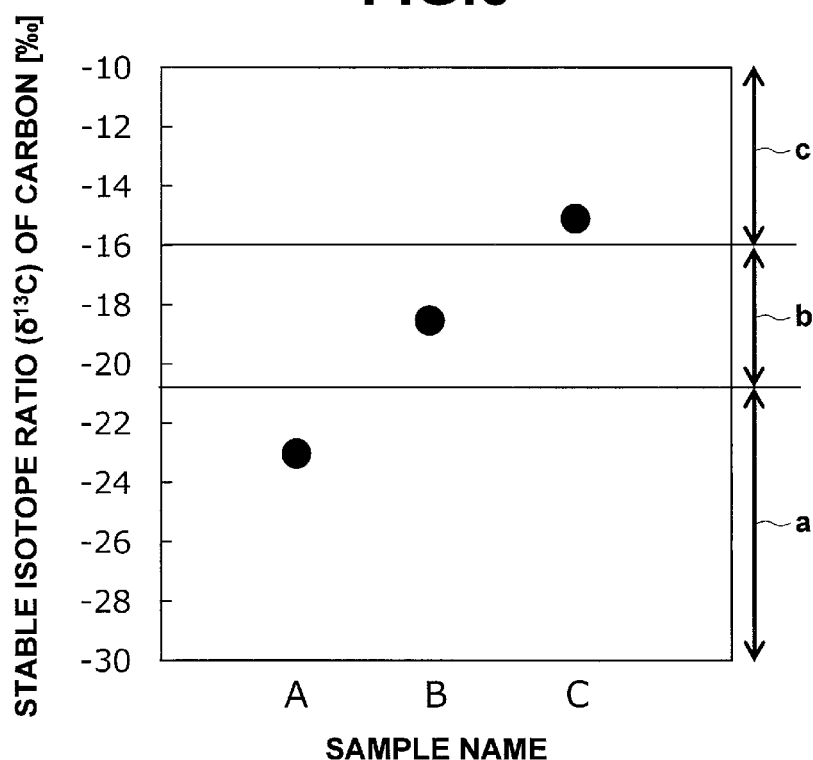
FIG. 6 is a graph showing the influence of feed on the stable isotope ratio of carbon contained in animal hair.

The abovementioned washing, drying, and degreasing processes are performed on each of these three types of samples A to C. The stable isotope ratio of carbon of each of the three types of samples A to C having undergone the washing, drying, and degreasing processes is analyzed by laser spectroscopic stable isotope ratio analysis. FIG. 6 shows the analytical results.

The stable isotope ratios of carbon increase in the order of samples A, B, and C. The difference between the stable isotope ratios of carbon of samples A and B is 5‰, and the difference between the stable isotope ratios of carbon of samples B and C is 3‰.

It is known that the stable isotope ratio of carbon of the C3 plant is smaller than the stable isotope ratio of carbon of the C4 plant. On the other hand, the stable isotope ratio of carbon of animal hair sample A of the animal eating the C3 plant as staple feed is smaller than the stable isotope ratio of carbon of animal hair sample C of the animal eating the C4 plant as staple feed. Also, the stable isotope ratio of carbon of animal hair sample B of the animal eating both the C3 and C4 plants as staple feed is intermediate between samples A and C. From the foregoing, there is a correlation between the type of feed and the stable isotope ratio of carbon of animal hair. Based on this correlation, it is possible to estimate feed eaten by an animal from which a measurement target object (animal hair) is collected, by measuring the stable isotope ratio of carbon contained in the measurement target object (animal hair).

When experiments of this kind were repetitively performed, the stable isotope ratio of carbon contained in the hair of the animal grown by the C3 plant was −21‰ or less (range a), the stable isotope ratio of carbon contained in the hair of the animal grown by the feed mixture containing the C3 and C4 plants was −21‰ to −16‰ (range b), and the stable isotope ratio of carbon contained in the hair of the animal grown by the C4 plant such as corn was −16‰ or less (range c).

Estimation of Geographical Origin from Stable Isotope Ratio of Hydrogen: Estimation Example 1

Figure 7:
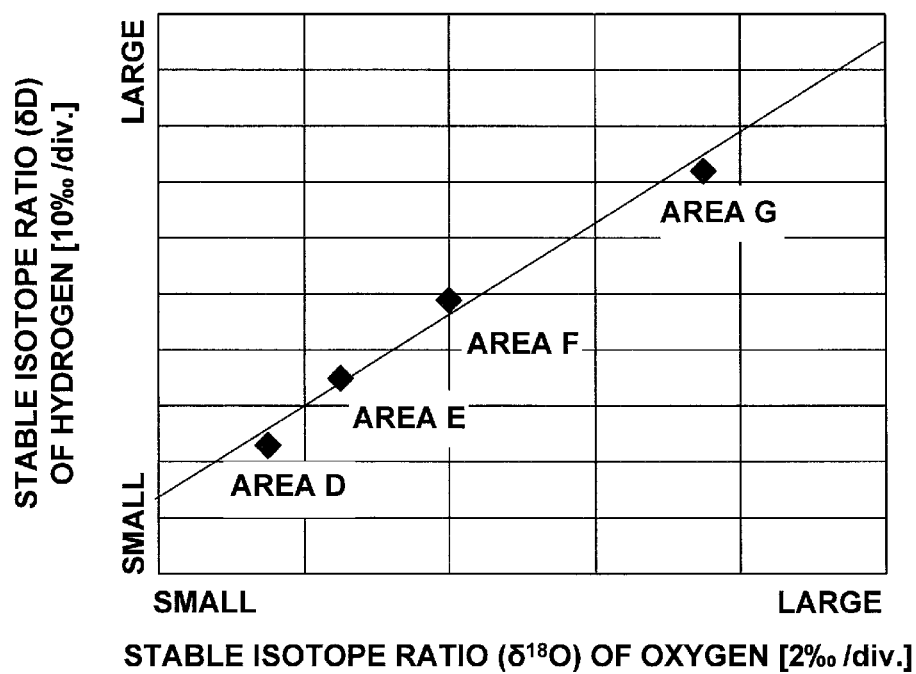
FIG. 7 is a graph showing the stable isotope ratios of oxygen and hydrogen contained in precipitation in different collection places.

For each of water samples D, E, F, and G of areas D, E, F, and G arranged in descending order of the latitude, the stable isotope ratios of hydrogen and oxygen are measured by laser spectroscopic stable isotope ratio analysis. First, water samples D to G are evaporated. The generated water vapor is irradiated with a laser beam. The stable isotope ratios of hydrogen and oxygen are measured by measuring and analyzing the laser beam absorption amount (the optical absorption intensity) by laser spectroscopy. FIG. 7 shows the measurement results.

As the latitude of the area increases, the stable isotope ratio ($\delta D$) of hydrogen and the stable isotope ratio ($\delta^{18}O$) of oxygen decrease. A straight line shown in FIG. 7 is called a global meteoric water line, and indicates an average relationship ($\delta D = 8 \times \delta^{18}O + 10‰$) between the stable isotope ratios of hydrogen and oxygen in relation to precipitation in the world. Water samples D to G of areas D to G are plotted on this straight line.

Figure 8:
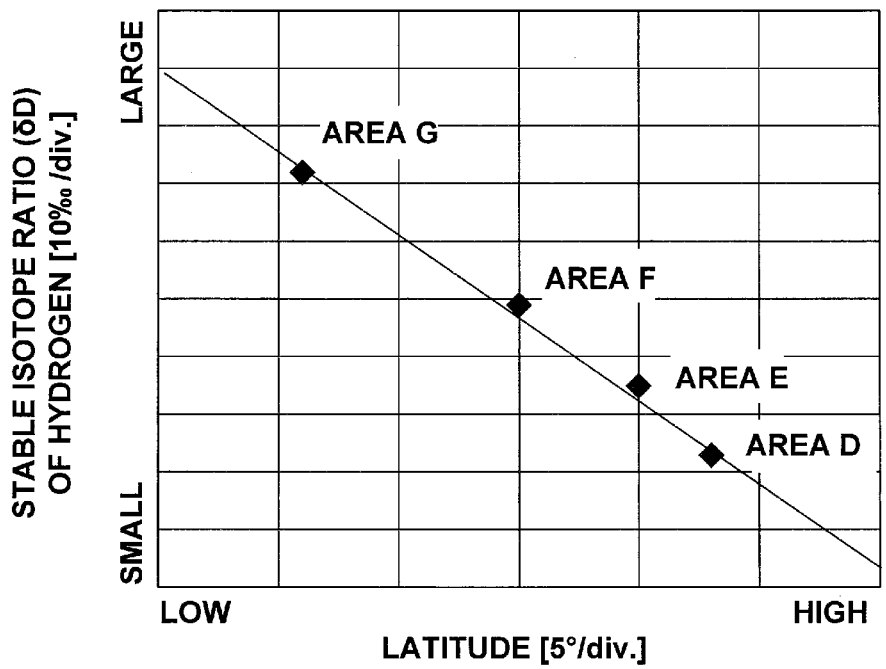
FIG. 8 is a graph showing the relationship between the stable isotope ratio of hydrogen contained in precipitation and the latitude of a collection place.

FIG. 8 shows the relationship between the stable isotope ratio of hydrogen and the latitude. As the latitude becomes higher, the stable isotope ratio of hydrogen becomes smaller. In areas D to G, the stable isotope ratio of hydrogen in precipitation decreases by 2.8‰ when the latitude increases by 1°.

Then, animal hair sample H of an animal grown in area H, animal hair sample I of an animal grown in area I, animal hair sample J of an animal grown in area J, and animal hair sample K of an animal grown in area K are prepared. The stable isotope ratio of hydrogen of each of these animal hair samples is measured by laser spectroscopic stable isotope ratio analysis.

Figure 9:
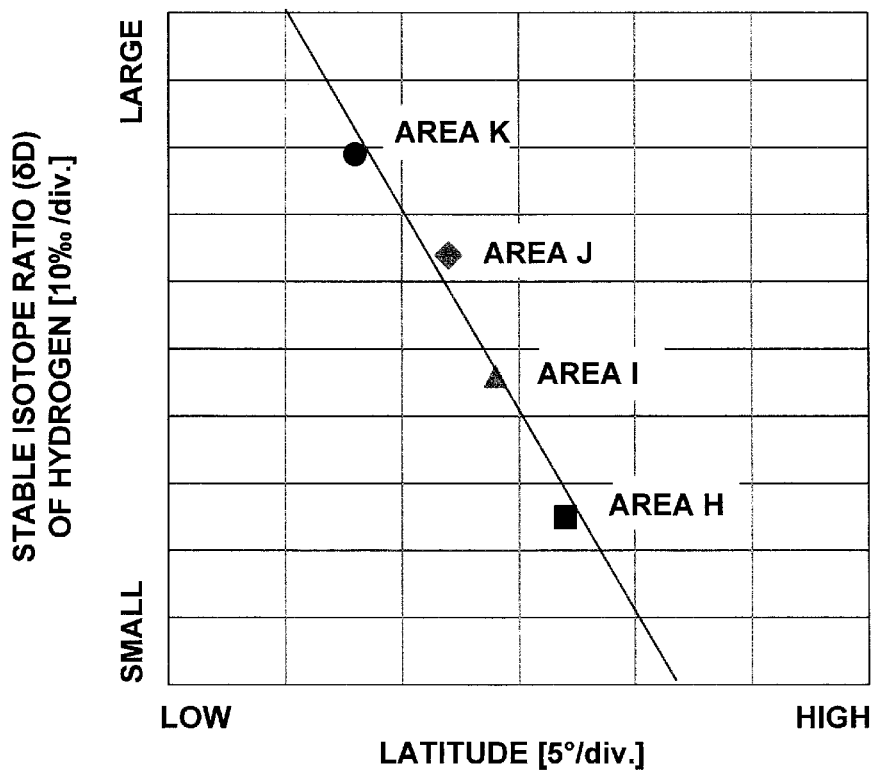
FIG. 9 is a graph showing the relationship between the stable isotope ratio of hydrogen contained in animal hair and the latitude of a collection place (geographical origin)

FIG. 9 shows the relationship between the measurement results of the stable isotope ratios of hydrogen contained in the animal hairs, and the latitudes of the growth areas of the animals from which the animal hair samples were collected. As shown in FIG. 9, the higher the latitude of the growth area, the smaller the stable isotope ratio of hydrogen contained in the animal hair, i.e., there is a correlation between them.

As shown in FIGS. 8 and 9, the higher the latitude of an area, the smaller the stable isotope ratio of hydrogen in precipitation. Since an animal grows by drinking water (precipitation) in the area, the stable isotope ratio of hydrogen contained in an organic substrate (e.g., keratin) forming the hair of an animal has a correlation with the stable isotope ratio of hydrogen of water in the area which the animal drank during the growth. As shown in FIG. 9, therefore, the stable isotope ratio of hydrogen contained in animal hair becomes smaller as the latitude of the area becomes higher. Based on this correlation, a rough area (the latitude) where an animal from which a measurement target object (animal hair) was collected has grown can be estimated by measuring the stable isotope ratio of hydrogen contained in the measurement target object (animal hair).

Estimation of Geographical Origin from Stable Isotope Ratio of Hydrogen: Estimation Example 2

<Difference $\Delta\delta$ Between Stable Isotope Ratios of Hydrogen Contained in Precipitation>

Assuming that an arbitrary point is a reference point, a difference $\Delta\delta$ between the stable isotope ratio of hydrogen contained in precipitation at this reference point and the stable isotope ratio of hydrogen contained in precipitation in an arbitrary area is represented by the sum of a difference $\Delta\delta A$ calculated from the latitude difference between the reference point and the arbitrary area and a difference $\Delta\delta B$ calculated from the altitude difference between the reference point and the arbitrary area (see, e.g., non-patent references 6 and 7).

The difference $\Delta\delta A$ calculated from the latitude difference is indicated by equation (3):

$$\Delta\delta A(‰)=-b\times\Delta Y \quad (3)$$

where $\Delta Y$ is the latitude difference (°), and b is a constant. In this equation, the constant b is 2.8 to 4.4 as a value suitable for cashmere geographical origin estimation.

The difference $\Delta\delta B$ calculated from the altitude difference is indicated by equation (4)

$$\Delta\delta B(‰)=-0.0065\times c\times\Delta Z \quad (4)$$

where $\Delta Z$ is the altitude difference (m), and c is a constant. In this equation, the constant c is 3.1.

From equations (3) and (4), the difference $\Delta\delta$ between the stable isotope ratios of hydrogen contained in precipitation at the reference point and in the arbitrary area is indicated by equation (5) below:

$$\Delta\delta(‰)=\Delta\delta A+\Delta\delta B=-b\times\Delta Y-0.0065\times c\times\Delta Z \quad (5)$$

Equation (5) represents that at a point at which the latitude differs by $\Delta Y$ from the reference point (an arbitrary point) and the altitude differs by $\Delta Z$ from the reference point, the stable isotope ratio of hydrogen contained in precipitation differs by $\Delta\delta$ from the reference point.

Equation Indicating Relationship Between $\Delta\delta$ and $\delta D$

The stable isotope ratios of hydrogen contained in animal hair samples collected from animals grown in a plurality of areas are measured. In the following explanation, the animals are cashmere goats, and the animal hairs (animal hair samples) collected from the animals are cashmere, unless otherwise specified.

From the latitude and the altitude of the geographical origin (an area where a cashmere goat has grown) of a collected animal hair sample when it is assumed that each of the latitude and the altitude of the reference point is 0°, the difference $\Delta\delta$ between the stable isotope ratio of hydrogen contained in precipitation at the reference point and the stable isotope ratio of hydrogen contained in precipitation of the geographical origin of the collected animal hair sample is calculated by using abovementioned equation (5). This calculation of the difference $\Delta\delta$ is performed for the geographical origins (the abovementioned plurality of areas) of all the animal hair samples for which the stable isotope ratio of hydrogen is measured.

Figure 10:
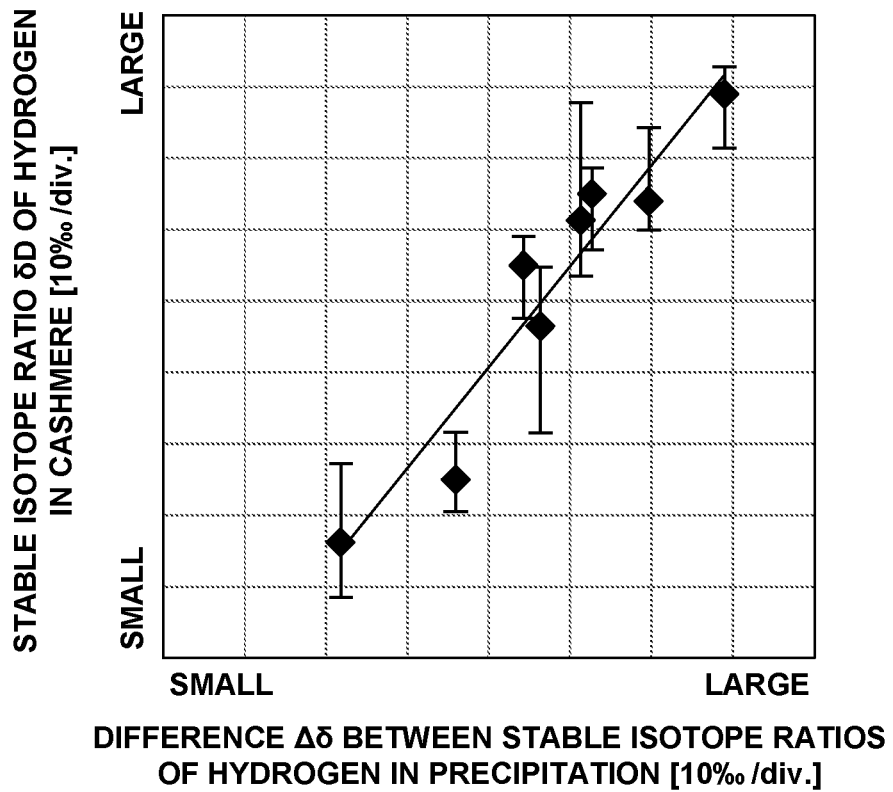
FIG. 10 is a graph for explaining the process of deriving an equation showing the relationship between a difference $\Delta\delta$ between the stable isotope ratio of hydrogen contained in precipitation at a reference point and the stable isotope ratio of hydrogen contained in precipitation in an estimation target area, and a stable isotope ratio $\delta D$ of hydrogen contained in cashmere collected from a cashmere goat grown in the estimation target area, in which the estimation target area is an area defined as a possible area where cashmere goats are growing.

A graph is formed by plotting the difference $\Delta\delta$ between the stable isotope ratios of hydrogen contained in precipitation at the reference point and in the animal hair sample geographical origin on the abscissa, and plotting the stable isotope ratio $\delta D$ of hydrogen contained in the animal hair sample for which the difference $\Delta\delta$ is calculated on the ordinate (see FIG. 10). Then, the least square method is used to derive equation (6) indicating the relationship between the difference $\Delta\delta$ between the stable isotope ratios of hydrogen contained in precipitation at the reference point and in the animal hair sample geographical origin, i.e., the relationship between the difference $\Delta\delta$ between stable isotope ratios of hydrogen contained in precipitation at the reference point and in an area (to be referred to as "an estimation target area" hereinafter) where an animal from which the animal hair sample was collected may have grown, and the stable isotope ratio $\delta D$ of hydrogen contained in the animal hair sample.

$$\delta D=\alpha\times\Delta\delta+\beta \quad (6)$$

where $\alpha$ and $\beta$ are constants.

Note that equation (6) is derived by using average values if the stable isotope ratios of hydrogen contained in animal hair samples of the same geographical origin vary, or if the stable isotope ratios of hydrogen contained precipitation in the same area vary.

Equation (7) is obtained by substituting equation (5) into equation (6):

$$\delta D=\alpha\times(-b\times\Delta Y-0.0065\times c\times\Delta Z)+\beta \quad (7)$$

$\delta D$ in equation (7) is a function of the latitude ($\Delta Y$) and the altitude ($\Delta Z$).

When deriving equation (7), data of stable isotope ratios of hydrogen in at least three areas is necessary. The number of areas is desirably as large as possible because the accuracy of the equation increases. In FIG. 10, data of eight areas is plotted.

When b=4.0 and c=3.1 in equation (7), $\alpha$=1.41 and $\beta$=198. That is, when b=4.0 and c=3.1, abovementioned equation (6) is represented by equation (6a):

$$\delta D=1.41\times\Delta\delta+198 \quad (6a)$$

Note that this calculation was performed by referring to the values of $\Delta\delta$ corresponding to the altitude, latitude, and longitude of the abovementioned area in a database (see, e.g., non-patent literature 8) disclosed on the Internet. However, it is also possible to actually measure the stable isotope ratio of hydrogen contained in precipitation collected in the growth area of a cashmere goat, and calculate the values of α and β in equation (6) by using the measured value.

<Geographical Origin Estimation Using Equation Indicating Relationship Between Δδ and δD>

A case in which a measurement target object is cashmere and whether the geographical origin of this cashmere is Chifeng in the Inner Mongolia Autonomous Region is discriminated will be explained below. The range of values which the stable isotope ratio of hydrogen contained in cashmere can take is calculated by substituting the latitude (ΔY) and the altitude (ΔZ) of Chifeng into equation (7). The stable isotope ratio of hydrogen contained in the measurement target object (cashmere) is measured. If the measured stable isotope ratio of hydrogen falls within the value range obtained by the calculation, it is determined that the geographical origin of the measurement target object can be Chifeng. If the stable isotope ratio falls outside the range, it is determined that the geographical origin of the measurement target object cannot be Chifeng.

Figure 11:
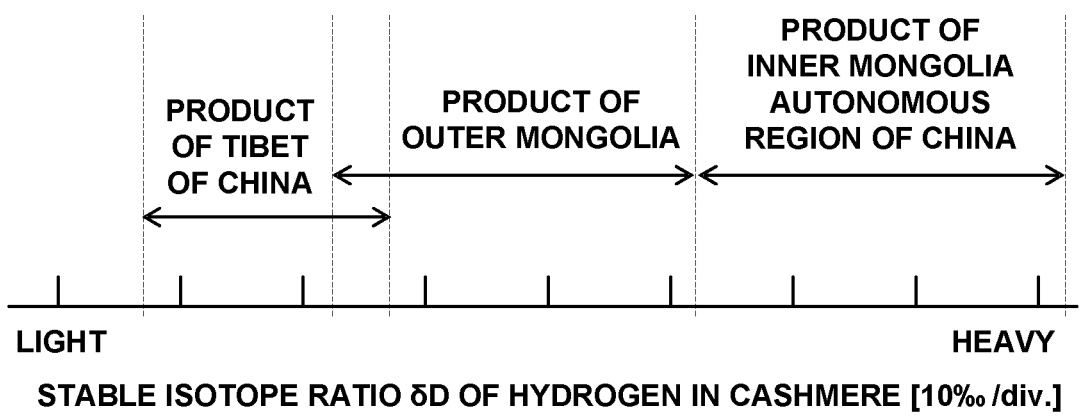
FIG. 11 is a graph showing the relationship between the stable isotope ratio of hydrogen contained in cashmere and the geographical origin.

In addition, for each of Outer Mongolia, Tibet of China, and the Inner Mongolia Autonomous Region of China known as cashmere geographical origins, the range of values which the stable isotope ratio δD of hydrogen contained in cashmere is calculated by substituting the latitude (ΔY) and the altitude (ΔZ) of the country or the area into equation (7). Consequently, as shown in FIG. 11, the range of the stable isotope ratio δD of hydrogen contained in cashmere is obtained for each geographical origin. In this example, the stable isotope ratio δD of hydrogen contained in cashmere changes from light (small) to heavy (large) in the order of Tibet of China, Outer Mongolia, and the Inner Mongolia Autonomous Region of China. The geographical origin of a measurement target object (cashmere) can be estimated by measuring the stable isotope ratio δD of hydrogen contained in the measurement target object, and checking the range within which the measured stable isotope ratio δD falls in FIG. 11.

Note that as described above, the values of α and β in equation (6) are obtained from the stable isotope ratio of hydrogen contained in each of precipitation (growth water) and cashmere collected in the growth area of a cashmere goat. The range of the stable isotope ratio δD of hydrogen contained in cashmere is also obtained for each geographical origin by using equation (6) in which the values of α and β are set, instead of equation (7). Accordingly, the geographical origin can be estimated by measuring the stable isotope ratio δD of hydrogen contained in a measurement target object (cashmere), and collating the measurement result with the ranges obtained by equation (6).

Narrowing-Down of Geographical Origins from Stable Isotope Ratios of Hydrogen and Carbon A method of estimating, from an animal hair sample as a measurement target object, the growth area (the geographical origin of animal hair) of an animal from which the animal hair sample was collected will be explained with reference to FIGS. 12 to 15.

Figure 13:
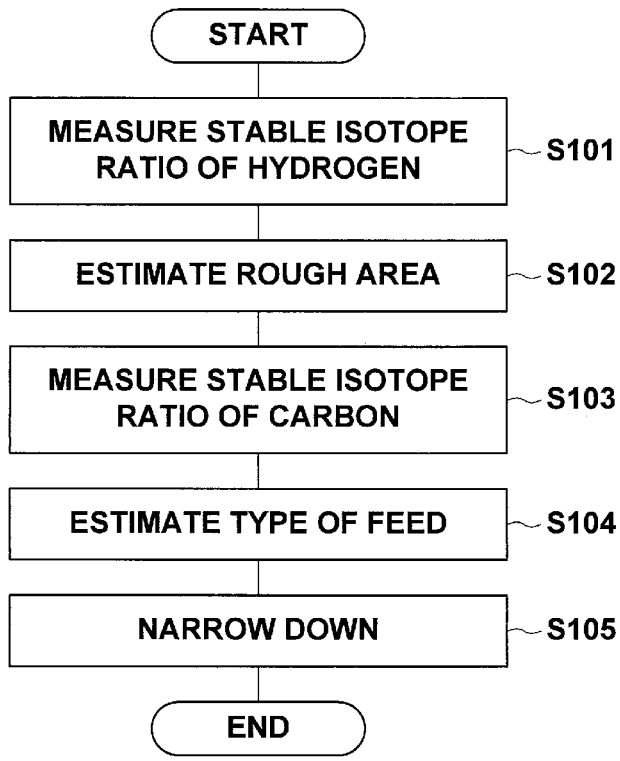
FIG. 13 is a flowchart showing the procedure of estimating a collection place (geographical origin) from the stable isotope ratios of hydrogen and carbon contained in animal hair.
Figure 14:
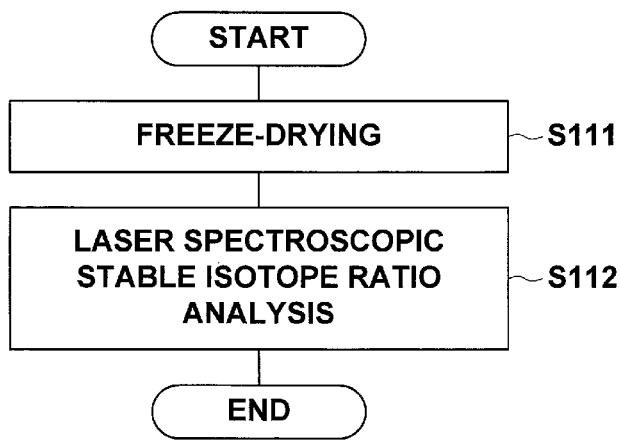
FIG. 14 is a flowchart showing a detailed procedure of measuring the stable isotope ratio of hydrogen contained in animal hair.
Figure 15:
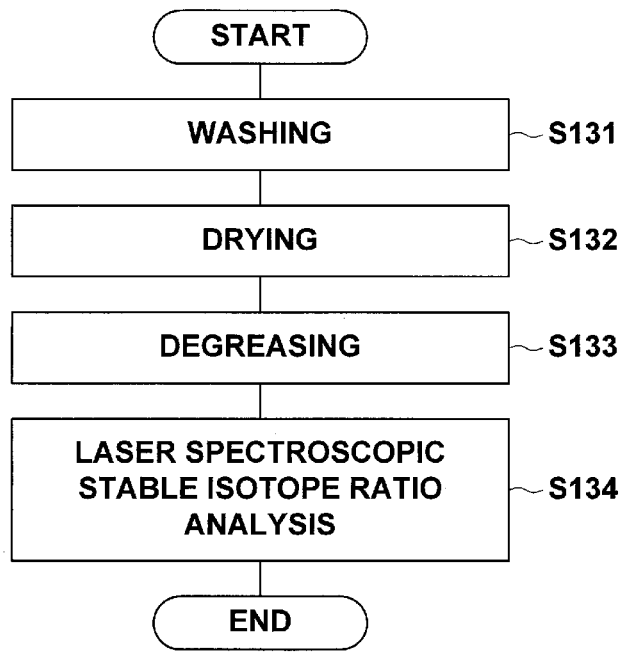
FIG. 15 is a flowchart showing a detailed procedure of measuring the stable isotope ratio of carbon contained in animal hair.

First, the stable isotope ratio of hydrogen contained in the animal hair sample is measured (step S101 in FIG. 13). More specifically, a freeze-drying process is performed on the animal hair sample (step S111 in FIG. 14). The stable isotope ratio of hydrogen contained in the freeze-dried animal hair sample is measured by laser spectroscopic stable isotope ratio analysis (step S112 in FIG. 14).

Figure 12:
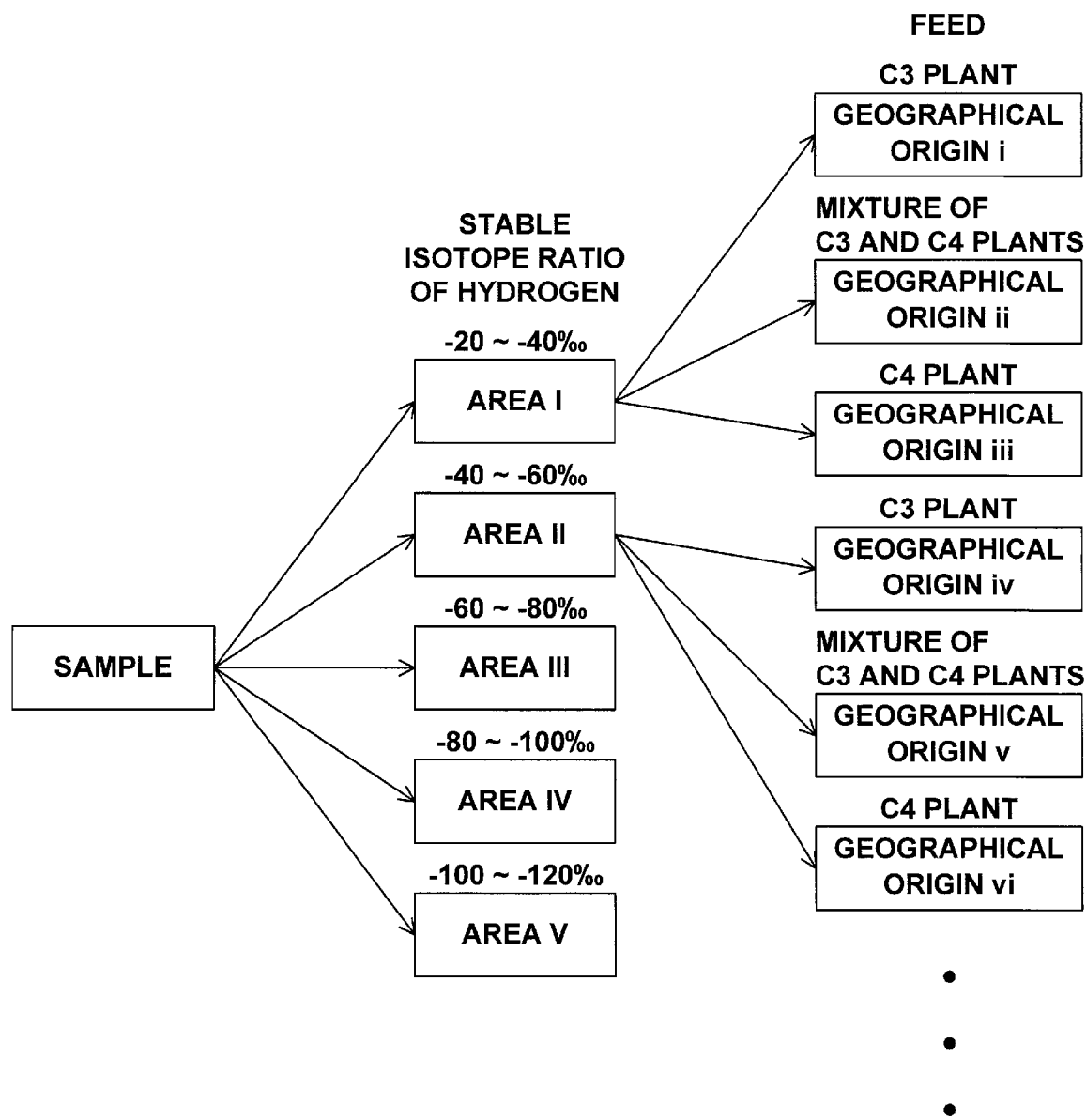
FIG. 12 is a view for explaining a procedure of estimating a collection place (geographical origin) from the stable isotope ratios of hydrogen and carbon contained in animal hair.

A rough area where an animal from which the animal hair sample was collected has grown is estimated from the measured stable isotope ratio of hydrogen (step S102 in FIG. 13). When adopting Estimation Example 1 described earlier, an arbitrary animal hair sample is classified into hairs of animals having grown in a plurality of areas in accordance with the range of the stable isotope ratio of hydrogen. For example, as shown in FIG. 12, the geographical origin of the animal hair sample is classified into five areas for each 20‰ of the stable isotope ratio of hydrogen. The geographical origin is area I when the stable isotope ratio of hydrogen is −20 to −40‰, area II when it is −40 to −60‰, area III when it is −60 to −80‰, area IV when it is −80 to −100‰, and area V when it is −100 to −120‰. When the stable isotope ratio of hydrogen in the animal hair sample is −100‰, it is estimated that the sample was collected in area IV.

When adopting Estimation Example 2 described previously, a rough area where an animal from which an animal hair sample was collected has grown is estimated from the equation (equation (6), (6a), or (7)) indicating the relationship between the difference Δδ between the stable isotope ratios of hydrogen contained in precipitation at a predetermined reference point and in an estimation target area (an area where an animal from which a measurement target object was collected may have grown), and the stable isotope ratio δD of hydrogen contained in an animal hair sample collected from the animal having grown in the estimation target area, and from the stable isotope ratio of hydrogen measured in step S101.

Then, the stable isotope ratio of carbon contained in the animal hair sample is measured (step S103 in FIG. 13). More specifically, the animal hair sample is washed with a neutral detergent (step S131 in FIG. 15). The washed animal hair sample is dried (step S132 in FIG. 15). The dried animal hair sample is degreased by being dipped in ethanol (step S133 in FIG. 15). The stable isotope ratio of carbon of the degreased sample is analyzed by laser spectroscopic stable isotope ratio analysis (step S134 in FIG. 15).

From the measured stable isotope ratio of carbon, the type of feed of the animal from which the animal hair sample was collected is estimated (step S104 in FIG. 13). In this case, whether the feed is a C3 plant, a C4 plant, or a feed mixture of the C3 and C4 plants is estimated.

Subsequently, the rough area estimated in step S102 is narrowed down to an area using the feed estimated in step S104, and it is estimated that this narrowed-down area is the growth area of the animal from which the animal hair sample was collected (step S105 in FIG. 13). For example, in FIG. 12, when it is estimated that the growth area is area I from the stable isotope ratio of hydrogen and that the feed is the C3 plant, an area in which the animal is grown by using grass of the C3 plant as feed in area I is narrowed down to geographical origin i. This increases the reliability of geographical origin estimation because the area (geographical origin) where the animal from which the animal hair sample was collected has grown is estimated by a narrower unit.

Figure 16:
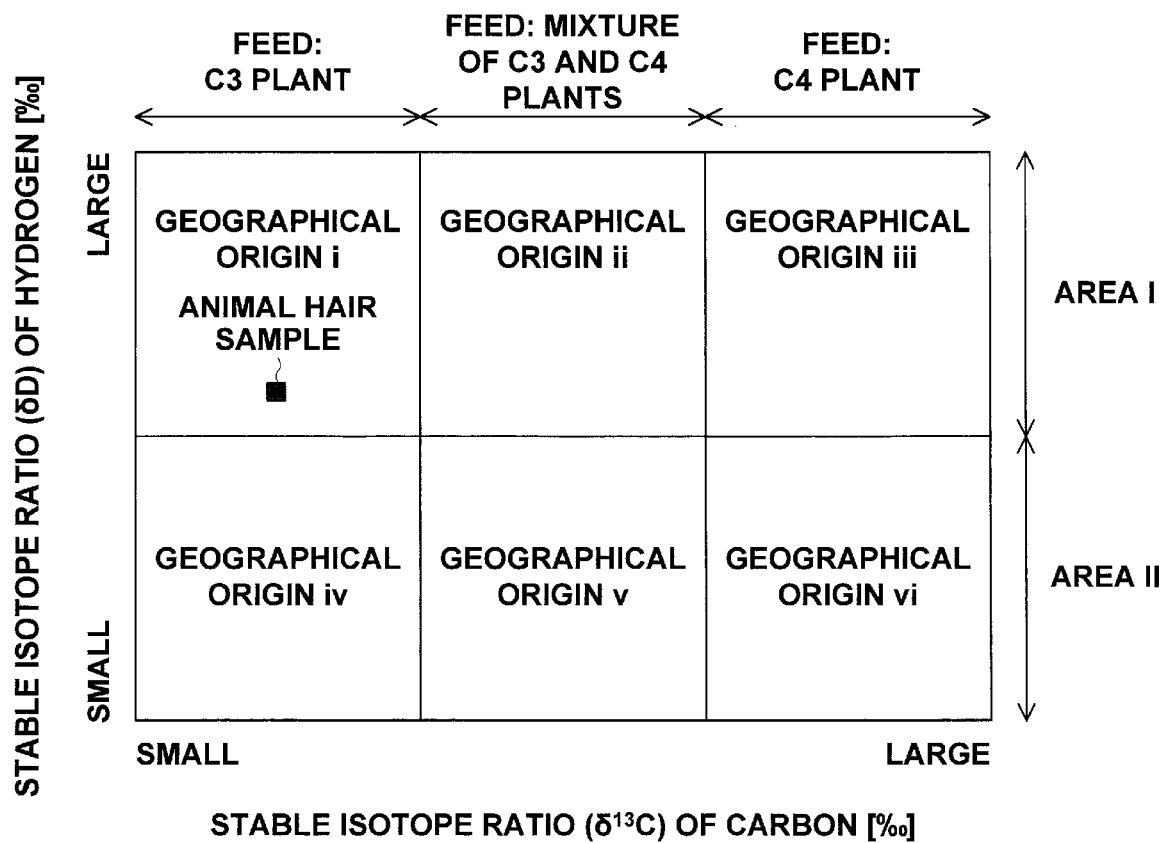
FIG. 16 is a view showing am example of the relationship between the stable isotope ratios of carbon and hydrogen contained in animal hair and the collection place (geographical origin)

FIG. 16 shows an example of the relationship between the stable isotope ratios of carbon and hydrogen contained in animal hair and the collection place (geographical origin). In the example explained with reference to FIGS. 12 to 15, the measurement result of the stable isotope ratio of hydrogen of the animal hair sample is included in the range of the stable isotope ratio of hydrogen of the hair of an animal grown in area I. Therefore, it is estimated that area I is a rough area where the animal from which the animal hair sample was collected has grown. In addition, the measurement result of the stable isotope ratio of carbon is included in the range of the stable isotope ratio of carbon of the hair of the animal grown by the feed C3. Accordingly, the growth area of the animal from which the animal hair sample was collected is narrowed down to geographical origin i.

Figure 17:
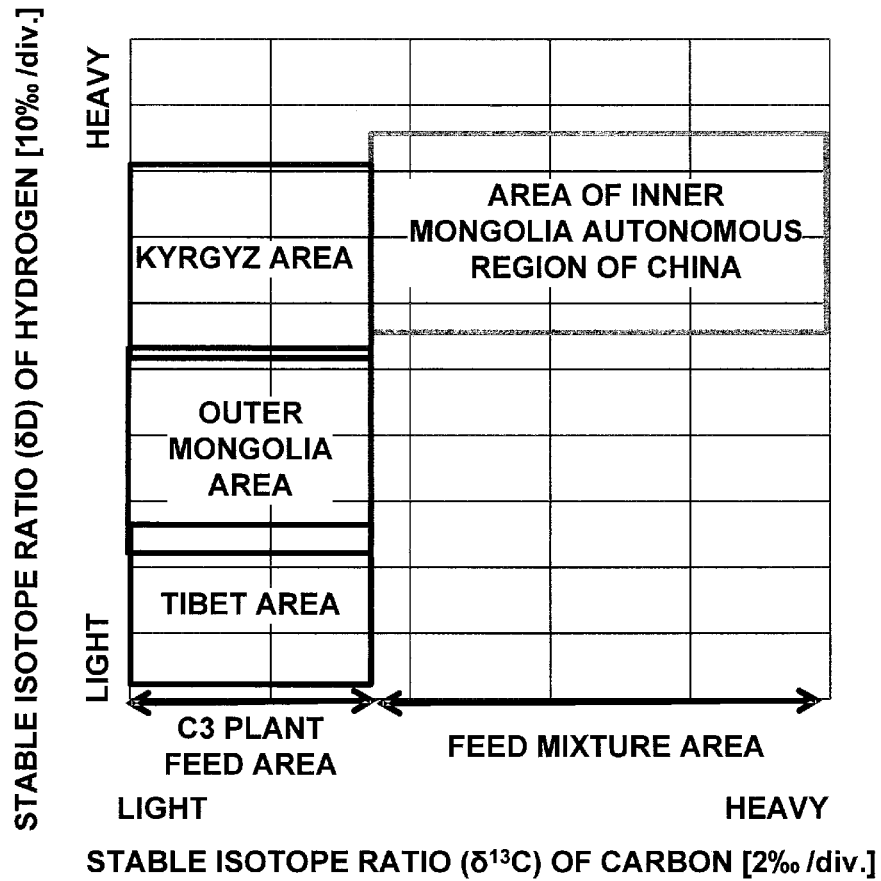
FIG. 17 is a view showing am example of the relationship between the stable isotope ratios of hydrogen and carbon contained in cashmere and the collection place (geographical origin)

FIG. 17 shows an example of the relationship between the stable isotope ratios of carbon and hydrogen contained in cashmere and the collection place (geographical origin). The range (a Kyrgyz area) of the stable isotope ratio of hydrogen of cashmere produced in Kyrgyz overlaps the range (an area of the Inner Mongolia Autonomous Region of China) of the stable isotope ratio of hydrogen of cashmere produced in the Inner Mongolia Autonomous Region of China. In this case, whether cashmere is produced in the Inner Mongolia Autonomous Region of China or Kyrgyz is determined by the value of the stable isotope ratio of carbon contained in cashmere.

That is, as shown in FIG. 17, cashmere goats growing in Kyrgyz mainly eat the C3 plant and hence are influenced by the stable isotope ratio of carbon of the C3 plant. On the other hand, cashmere goats growing in the Inner Mongolia Autonomous Region of China eat both the C3 and C4 plants and hence are influenced by the stable isotope ratio of carbon between the C3 and C4 plants. Consequently, whether cashmere is produced in the Inner Mongolia Autonomous Region of China or Kyrgyz can be determined from the value of the stable isotope ratio of carbon contained in the cashmere.

In an actual process, the stable isotope ratios of carbon and hydrogen of a plurality of animal hair samples whose geographical origins are already known are measured, and a table showing the relationship between the stable isotope ratios of carbon and hydrogen and the collection place (geographical origin) as shown in FIG. 16 or 17 is formed. Then, the stable isotope ratios of carbon and hydrogen of animal hair whose geographical origin is unknown are measured, and the measurement results are collated with the table as shown in FIG. 16 or 17, thereby estimating the area (geographical origin) where the animal from which the hair was collected has grown.

Use of Stable Isotope Ratio of Oxygen

FIG. 7 shows that the stable isotope ratios of hydrogen and oxygen in precipitation are proportional to each other. Since the stable isotope ratio of hydrogen of animal hair has a correlation with water (precipitation) drunk by an animal having the hair, the stable isotope ratio of oxygen of animal hair also has a correlation with the stable isotope ratio of oxygen in precipitation of an area in which the animal has grown. Like the stable isotope ratio of hydrogen of animal hair, therefore, the growth area of an animal can be estimated from the stable isotope ratio of oxygen.

Use of Laser Spectroscopy

The methods of stable isotope ratio analysis include IRMS (Isotope Ratio Mass Spectrometry) and NMR (Nuclear Magnetic Resonance Spectroscopy). Unfortunately, these methods require large expensive measurement apparatuses requiring complicated operations, and hence take a long time and a high cost. This makes it difficult to introduce stable isotope ratio analysis as a testing item in a distribution process in a city.

In this embodiment, therefore, a laser spectroscopic stable isotope ratio analyzer can be used when measuring the stable isotope ratios of oxygen, hydrogen, and carbon. This laser spectroscopic stable isotope ratio analyzer can easily analyze the stable isotope ratios of oxygen, hydrogen, and carbon contained in a measurement target object by irradiating a carbon dioxide gas and water vapor generated by burning the measurement target object with a laser beam, and analyzing the absorption amount of the laser beam (see, e.g., non-patent literature 5).

The laser spectroscopic stable isotope ratio analyzer is inexpensive, compact, and easy to operate when compared to the measurement apparatuses of IRMS and NMR. In addition, chemical pre-processes required for stable isotope ratio analysis by IRMS are unnecessary, so geographical origin estimation can be performed within a short time (e.g., within 1 hr). Accordingly, the use of the laser spectroscopic stable isotope ratio analyzer can reduce the time and the cost. Note that the laser spectroscopic stable isotope ratio analyzer can also be used in only one of the measurement of the stable isotope ratios of oxygen/hydrogen, and the measurement of the stable isotope ratio of carbon.

Determination of Validity of Geographical Origin Label from Stable Isotope Ratio of Hydrogen FIG. 9 shows that the stable isotope ratio of hydrogen of animal hair decreases by 6‰ when the latitude of the growth area of the animal increases by 1°. Letting Y be the stable isotope ratio of hydrogen of animal hair whose geographical origin (a latitude X') is certain, the relationship between the latitude (X) of the geographical origin and the stable isotope ratio (Y) of hydrogen of another animal hair sample can be represented by equation (8):

$$Y = -6 \times (X - X') + Y' \qquad (8)$$

When the stable isotope ratio (Y) of hydrogen of animal hair whose geographical origin (the latitude X') is certain is obtained as basic data, whether the geographical origin label of arbitrary animal hair is correct can be determined. First, the stable isotope ratio (Y) of hydrogen of arbitrary animal hair is measured. Then, the latitude (X) is obtained by substituting the value (Y) into equation (8). If the obtained latitude (X) matches the value of the latitude of the geographical origin indicated by the label, it is possible to determine that the geographical origin label is correct.

Estimation of Staple Feed from Stable Isotope Ratio of Carbon

When the stable isotope ratio of carbon contained in animal hair is smaller than −21‰ (range a in FIG. 6), it is estimated that the staple feed of an animal having the animal hair is a C3 plant. When the stable isotope ratio of carbon contained in animal hair is −21‰ to −16‰ (range b in FIG. 6), it is estimated that the staple feed of an animal having the animal hair is a feed mixture of the C3 plant and a C4 plant. When the stable isotope ratio of carbon contained in animal hair is larger than −16‰ (range c in FIG. 6), it is estimated that the staple feed of an animal having the animal hair is the C4 plant.

Application to Computer

Figure 18:
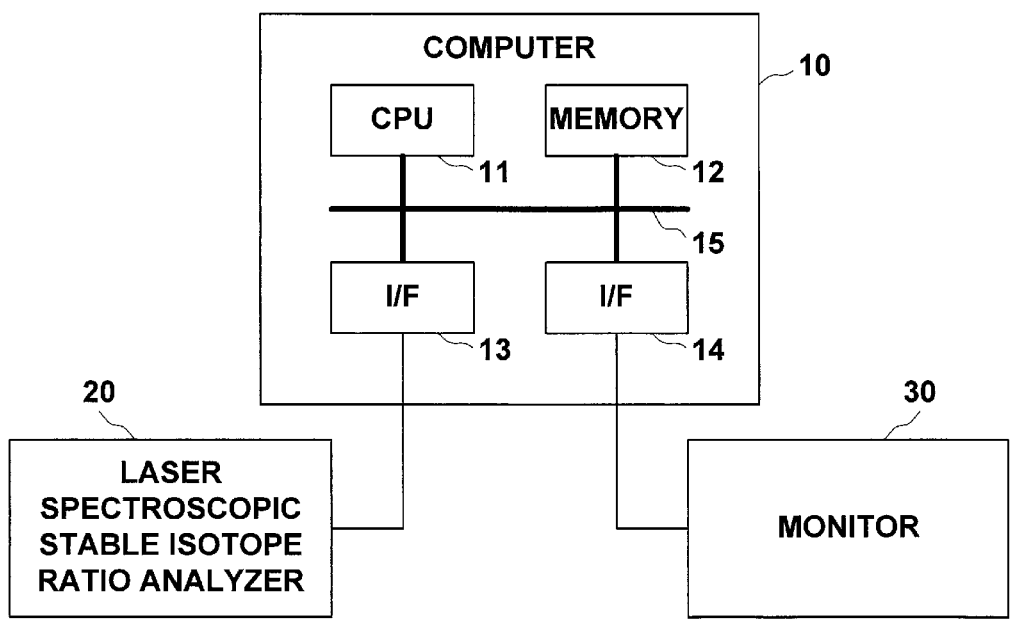
FIG. 18 is a block diagram showing the arrangement of a geographical origin estimation apparatus.

The above described geographical origin estimation method can also be performed by using a computer. As shown in FIG. 18, a computer 10 includes a CPU 11, a memory 12, and input/output interfaces (I/F) 13 and 14. These circuits are connected to each other by a bus 15.

A laser spectroscopic stable isotope ratio analyzer 20 is connected to the input/output interface 13. The laser spectroscopic stable isotope ratio analyzer 20 sequentially outputs the measurement results of the stable isotope ratio of hydrogen or oxygen and the stable isotope ratio of carbon contained in a measurement target object (animal hair) to the computer 10. Note that when the laser spectroscopic stable isotope ratio analyzer 20 is not connected to the computer 10, an operator may also manually input the measurement results to the computer 10. A monitor 30 is connected to the input/output interface 14.

A program necessary to execute step S3 in FIG. 1, steps S31 to S33 in FIG. 2, or steps S102, S104, and S105 in FIG. 13 is recorded in the memory 12. The CPU 11 operates in accordance with the program recorded in the memory 12, and estimates an area where an animal from which a measurement target object was collected has grown from the measurement results of the stable isotope ratios of the individual elements. The CPU 11 can also determine whether the geographical origin label of the measurement target object is correct. The CPU 11 displays these estimation results on the monitor 30.

Extension of Embodiment

The embodiment of the present invention has been explained above, but the present invention is not limited to the above embodiment. Various changes understandable by those skilled in the art within the technical scope of the present invention can be made on the arrangements and details of the invention.

For example, as described above, when measuring the stable isotope ratios of hydrogen and carbon, it is possible to obtain more accurate measurement results and estimate a geographical origin more reliably by performing the pre-processes (steps S111 and S131 to S133). However, these pre-processes may also be omitted if rough estimation results need only be obtained.

Also, the case in which the geographical origin of animal hair, particularly, cashmere hair as a measurement target object is estimated has been explained. However, embodiments of the present invention is also usable when estimating, e.g., the geographical origin of wool.

EXPLANATION OF THE REFERENCE NUMERALS AND SIGNS

10 . . . computer, 11 . . . CPU, 12 . . . memory, 13, 14 . . . input/output interface, 15 . . . bus, 20 . . . laser spectroscopic stable isotope ratio analyzer, 30 . . . monitor.

The invention claimed is:

1. A geographical origin estimation method comprising:
   measuring a stable isotope ratio of carbon contained in a measurement target object collected from an animal;
   measuring a stable isotope ratio of a constituent element of water contained in the measurement target object; and
   estimating an area where the animal has grown based on the stable isotope ratio of carbon and the stable isotope ratio of the constituent element of water;
   wherein estimating the area where the animal has grown comprises:
      estimating a rough area where the animal has grown from the stable isotope ratio of the constituent element of water;
      estimating feed used to grow the animal from the stable isotope ratio of carbon; and
      narrowing down the rough area to an area using the feed estimated from the stable isotope ratio of carbon; and
      estimating that the area using the feed is the area where the animal has grown; and
   wherein estimating the rough area comprises estimating the rough area from the stable isotope ratio of the constituent element of water according to an equation, the equation indicating a relationship between a difference $\Delta\delta$ and a stable isotope ratio $\delta D$, the difference $\Delta\delta$ being between a stable isotope ratio of a constituent element of water contained in precipitation at a predetermined reference point and a stable isotope ratio of a constituent element of water contained in precipitation in an estimation target area, and the stable isotope ratio $\delta D$ being of a constituent element of water contained in a measurement target object collected from an animal having grown in the estimation target area.

2. The geographical origin estimation method according to claim 1, wherein measuring the stable isotope ratio of carbon contained in the measurement target object comprises:
   washing the measurement target object with a neutral detergent;
   drying the measurement target object after washing the measurement target object;
   performing a degreasing process by dipping the measurement target object in ethanol after drying the measurement target object; and
   measuring the stable isotope ratio of carbon contained in the measurement target object after the degreasing process.

3. The geographical origin estimation method according to claim 1, wherein measuring the stable isotope ratio of the constituent element of water contained in the measurement target object comprises:
   freeze-drying the measurement target object; and
   measuring the stable isotope ratio of the constituent element of water contained in the measurement target object while the measurement target object is freeze-dried.

4. The geographical origin estimation method according to claim 1, wherein the equation is:

$$\delta D = 1.41 \times \Delta\delta + 198.$$

5. The geographical origin estimation method according to claim 1, wherein measuring the stable isotope ratio of carbon or measuring the stable isotope ratio of the constituent element of water comprises using a laser spectroscopic stable isotope ratio analyzer configured to:
   analyze a stable isotope ratio of carbon or the constituent element of water contained in the measurement target object by irradiating a carbon dioxide gas and water vapor generated by burning the measurement target object with a laser beam; and
   analyzing an absorption amount of the laser beam.

6. The geographical origin estimation method according to claim 1, wherein the measurement target object is animal hair.

7. The geographical origin estimation method according to claim 1, wherein the measurement target object is hair of a cashmere goat.

8. The geographical origin estimation method according to claim 1, wherein the constituent element of water is hydrogen.

9. The geographical origin estimation method according to claim 1, wherein the constituent element of water is oxygen.

* * * * *